United States Patent
Pollino et al.

(10) Patent No.: US 10,954,359 B2
(45) Date of Patent: Mar. 23, 2021

(54) HYDROXYBENZOPHENONE-BASED STABILIZERS AND POLYMERS END-CAPPED WITH THE SAME

(71) Applicant: SOLVAY SPECIALTY POLYMERS USA, LLC, Alpharetta, GA (US)

(72) Inventors: Joel Pollino, John Creeks, GA (US); Satchit Srinivasan, Dallas, TX (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 61 days.

(21) Appl. No.: 16/515,190

(22) Filed: Jul. 18, 2019

(65) Prior Publication Data

US 2019/0338105 A1 Nov. 7, 2019

Related U.S. Application Data

(62) Division of application No. 15/508,323, filed as application No. PCT/EP2015/070191 on Sep. 3, 2015, now Pat. No. 10,400,087.

(60) Provisional application No. 62/046,011, filed on Sep. 4, 2014.

(51) Int. Cl.
| | | |
|---|---|---|
| *C07C 317/22* | (2006.01) | |
| *C08K 5/41* | (2006.01) | |
| *C08G 65/48* | (2006.01) | |
| *C08G 75/23* | (2006.01) | |
| *C08G 85/00* | (2006.01) | |
| *C08L 81/06* | (2006.01) | |
| *C07C 315/04* | (2006.01) | |
| *C08G 75/20* | (2016.01) | |

(52) U.S. Cl.
CPC .............. *C08K 5/41* (2013.01); *C07C 315/04* (2013.01); *C07C 317/22* (2013.01); *C08G 65/48* (2013.01); *C08G 75/20* (2013.01); *C08G 75/23* (2013.01); *C08G 85/004* (2013.01); *C08L 81/06* (2013.01)

(58) Field of Classification Search
CPC ... C08F 2810/40; C08C 19/20; C08G 85/004; C07C 315/04; C07C 317/22; C07C 317/24

See application file for complete search history.

(56) References Cited

U.S. PATENT DOCUMENTS

| | | | |
|---|---|---|---|
| 3,192,179 A | | 6/1965 | Spatz et al. |
| 3,391,110 A | | 7/1968 | Coleman |
| 3,808,278 A | | 4/1974 | Avar et al. |
| 4,108,837 A | | 8/1978 | Johnson et al. |
| 4,517,354 A | * | 5/1985 | D'Alelio ............... C07C 317/00 528/171 |
| 4,710,562 A | * | 12/1987 | Maresca .............. C08G 61/127 525/390 |
| 6,537,670 B1 | * | 3/2003 | Sassi ...................... C07C 69/36 428/412 |

FOREIGN PATENT DOCUMENTS

JP S5032146 3/1975

OTHER PUBLICATIONS

Finocchiaro, Macromol. Chem. Phys. 197, 1007-1019 (1996) (Year: 1996).*

"Colquhoun, Howard M. et al., ""Synthesis of Strained Macrocyclic Biaryls for Enthalpy-Driven Ring-Opening Polymerization"", Macromolecules, 2005, vol. 38, No. 25, pp. 10413-10420—American Chemical Society."

* cited by examiner

*Primary Examiner* — Robert C Boyle

(57) ABSTRACT

The invention relates to hydroxybenzophenone-based compounds of formula (I) that are used to improve UV, thermal, and thermo-oxidative stability of high performance aromatic polymers in a blend or as end-cappers of the same polymers.

11 Claims, No Drawings

HYDROXYBENZOPHENONE-BASED STABILIZERS AND POLYMERS END-CAPPED WITH THE SAME

CROSS-REFERENCE TO RELATED APPLICATIONS

This application claims priority to U.S. provisional patent application No. 62/046,011 filed Sep. 4, 2014, the whole content of this application being incorporated herein by reference for all purposes.

FIELD OF THE INVENTION

The invention relates to 2-hydroxybenzophenone-based compounds that are used to stabilize oligomers and/or polymers. These compounds, referred to herein as stabilizer compounds (SC), can be used in blends with polymers or as polymer/oligomers end-cappers. The resultant blends or cod-capped polymers (referred to as end-capped stabilized polymers (ESP)) provide improved UV stability. The disclosure further relates to methods of synthesizing the stabilizer compounds (SC) and end-capped stabilized polymers (ESP), polymer composition (C) including these stabilizer compounds (SC), or end-capped stabilized polymers (ESP), and articles made from such polymers compositions (C).

BACKGROUND AND RELATED ART

High performance aromatic polymers feature, because of their very high glass transition temperatures and/or melting temperatures, excellent properties including an outstanding heat resistance. Aromatic polysulfones and polyetherketones are, for example, widely used in applications where their strength, resistance to harsh chemicals and to high temperatures is necessary.

Unfortunately, many natural and synthetic polymers such as the above mentioned high performance aromatic polymers are prone to light absorption and are attacked by UV radiation. As a result, they undergo oxidation, chain scission, uncontrolled radical recombination and cross-linking reactions. This phenomenon, known as UV degradation, is usually catalyzed in high heat environments in the presence of oxygen. The UV degradation of polymers can affect a materials mechanical properties, produce discoloration and fading, roughen the surface, decrease tensile strength, and reduce their overall life time performance.

A wide range of light and heal stabilizers for polymers are known and have been used alone or in various combinations to prevent or retard the kinetics of polymer degradation that is initiated by exposure to light and heat. The effectiveness of stabilizers to defend a material against UV radiation and heat depends on several factors including: the intrinsic efficacy of the stabilizer, its concentration, and its solubility in a particular polymer matrix, as well as how well it is distributed in the matrix. Intrinsic volatility of the stabilizer is also an important factor to consider when working with materials which are processed at high temperatures as it may lower the concentration of the stabilizer in a particular polymer matrix as a result of evaporation during processing and subsequent use.

Over the past century, a number of light stabilizer compounds have also been developed and commercialized as additives tailored to retard or eliminate photo-initiated oxidative processes. These additives are generally categorized into one of 4 classes: UV absorbers, excited state quenchers, radical scavengers, and peroxide decent posers. Certain derivatives of 2-hydroxybenzophenone have been known for a long time to improve the light stability of polymeric compositions. For example, U.S. Pat. No. 3,192,179 discloses their use in low melting temperature polymeric materials such as certain polyester-styrene resins and polyvinyl chloride resin.

Nearly all commercially available heat and light stabilizers are indeed well suited for blending with low melting temperature commodity polymers requiring low process temperatures (i.e. below 25° C.).

However, such commercial heat and light stabilizers are prone to thermo-oxidative decomposition or volatilization upon exposure to high temperatures (i.e. above 250° C.). Therefore, they are generally poorly suited for high performance aromatic polymers where process temperatures are substantially more intense compared to low melting temperature commodity polymers.

There exists a need, therefore, to identify and develop stabilizer compounds that are well suited for high performance aromatic polymers in that the polymer compositions made therefrom possess high temperature mechanical performance, good thermal-oxidative stability and good light stability.

The present invention provides such stabilizer compounds (SC), end-capped stabilized polymers (ESP), and methods for their preparation and use.

SUMMARY

The present invention relates to a stabilizer compound (SC) of the general structural formula (I):

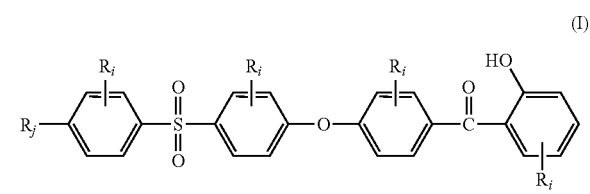

wherein:

$R_j$, same or different from $R_i$, is selected from:
  a first group consisting of a —H, a halogen, a carboxylic ester, an acid halide, an anhydride, an amide, and a thioester,
  a second group consisting of a hydroxyl, an amine, a carboxylic acid, a thiol, and any protected derivatives thereof.
  a moiety of formula (II):

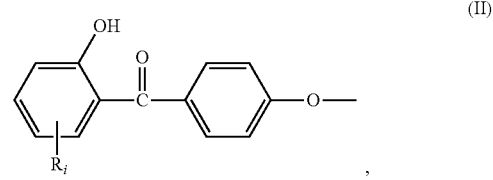

a moiety of formula (II*):

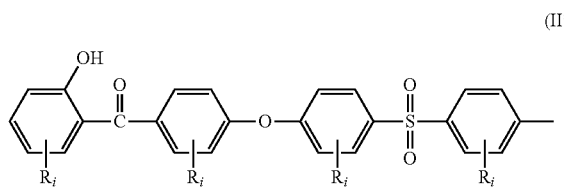

and $R_i$, same or different from each other and from $R_j$, are selected from the group consisting of —H, —NO$_2$, alkyl groups, alkoxy groups, perfluorinated groups, aryl groups, aryl amine groups, aryl ether groups, aryl sulfone groups, aryl thioether groups, and fused aryl ring systems.

Another aspect of the present invention relates to a method for the manufacture of said stabilizer compound (SC).

Still another aspect of the present invention is directed to an end-capped stabilized polymer (ESP) comprising recurring units and at least two chain ends, wherein at least one of the chain ends comprises the moiety of the general structural formula (X):

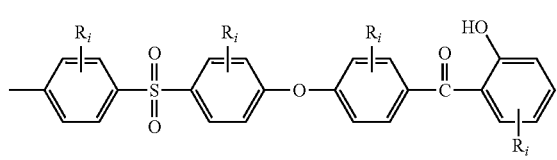

wherein $R_i$ are as defined above.

Yet another aspect of the present invention relates to a method for the manufacture of said end-capped stabilized polymer (ESP).

Still another aspect of the present invention is directed to a polymer composition (C) comprising at least one stabilizer compound (SC) or at least one end-capped stabilized polymer (ESP) and at least one polymer (P*), different from the end-capped stabilized polymer (ESP).

Yet another aspect of the present invention relates to a method for stabilizing a polymer (P) or (P*) comprising adding at least one stabilizer compound (SC) or at least one end-capped stabilized polymer (ESP) to at least one polymer (P) or to at least one polymer (P*), wherein the polymer (P), contains at least one chain end able to react with the above mentioned $R_j$ of formula (I), and wherein the polymer (P*) may be the same than the polymer (P), except for the fact that it does not have to (but may) contain at least one chain end able to react with the $R_j$ of formula (I).

Finally, the present invention also relates to an article comprising said stabilizer compound (SC), said end-capped stabilized polymer (ESP) or said polymer composition (C).

DETAILED DESCRIPTION

The Applicant has discovered that stabilizer compounds (SC) of the general structural formula (I):

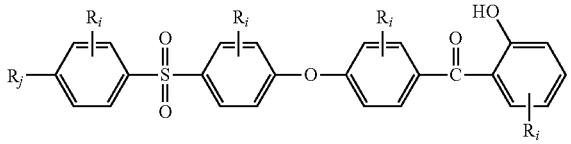

wherein $R_i$ and $R_j$ are as above defined, provide to high performance aromatic polymers very good light resistance.

In the formula (I), $R_j$ is preferably selected from:
- a first group consisting of a —H, a halogen, an acid halide and, an anhydride,
- a second group consisting of a hydroxyl, an amine, a carboxylic acid, and any protected derivatives thereof, or
- a moiety of formula (II):

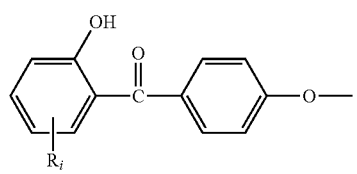

or
a moiety of formula (II*):

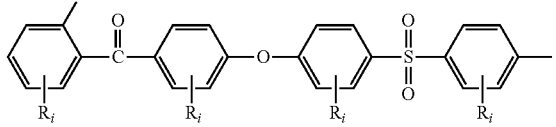

and
where $R_i$ is as above defined. In the formulas (II) and (II*), $R_i$ is preferably —H.

It may sometime be advantageous to select $R_j$ among the above mentioned second group, i.e. where $R_j$ can be a hydroxyl (or any protected derivative thereof), an amine (or any protected derivative thereof), a carboxylic acid (or any protected derivative thereof), or a thiol (or any protected derivative thereof).

In certain preferred embodiment, $R_j$ is selected from a halogen. Most preferably, it is selected from —Cl and —F.

In other preferred embodiments, $R_j$ is a hydroxyl or an amine or any protected derivatives thereof.

In the formula (I), $R_i$ are selected from the group consisting of —H, —NO$_2$, alkyl groups, alkoxy groups, perfluorinated groups, aryl groups, aryl amine groups, aryl ether groups, aryl sulfone groups, aryl thioether groups, and fused aryl ring systems.

Non limitative examples of alkyl groups are notably:

—CH$_3$, —CH$_2$CH$_3$, —CH$_2$CH$_2$CH$_3$, —CH(CH$_3$)$_2$,

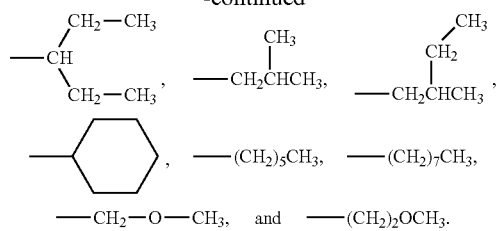

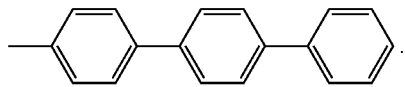

Non limitative examples of aryl amine groups are notably:

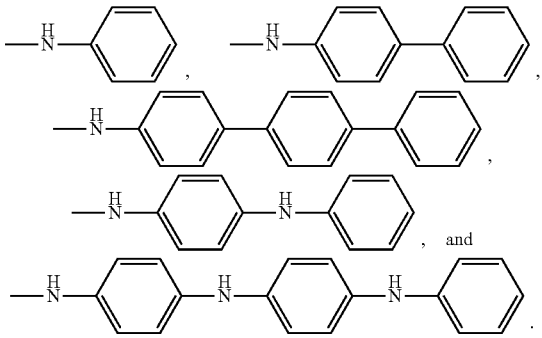

Non limitative examples of alkoxy groups are notably: —OCH₃, and —O(CH₂)ₙCH₃, where n=1 to 11.

Non limitative examples of perfluorinated groups are notably: —CF₃, and —CH₂—(CF₂)₅CF₃.

Non-limiting examples of aryl groups are notably:

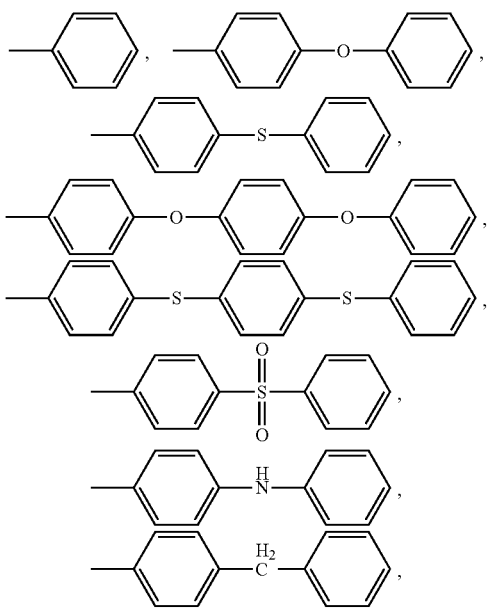

Non limitative examples of aryl groups are notably:

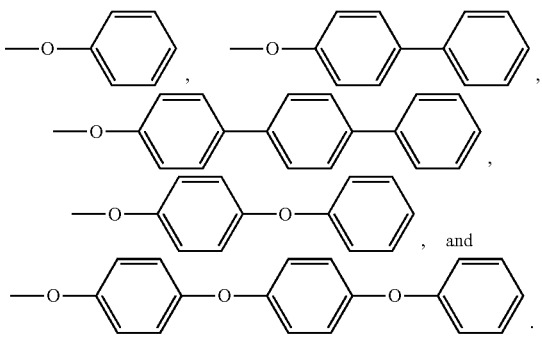

Non limitative examples of aryl sulfone groups are notably:

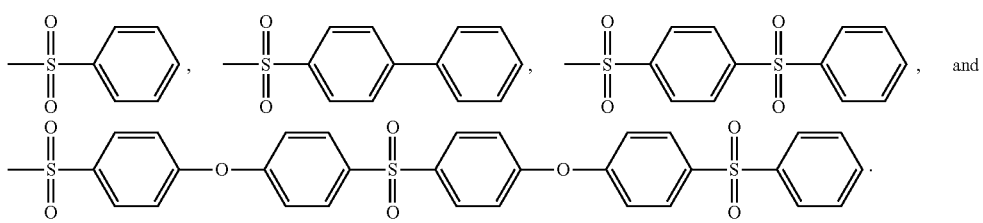

-continued

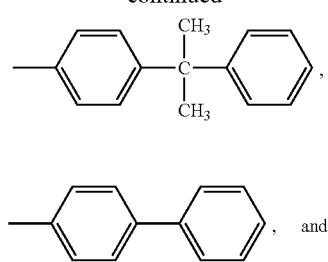

Non limitative examples of aryl thioether groups are notably:

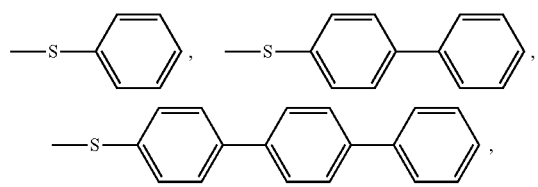

-continued

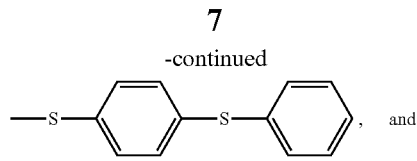, and

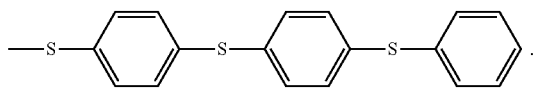.

Non limitative examples of fused aryl ring systems are notably:

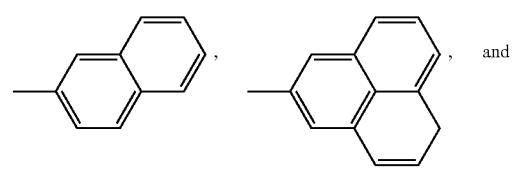, and

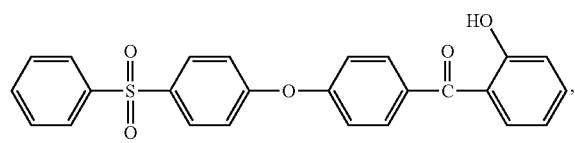.

$R_i$ is preferably selected from —H alkyl groups, alkoxy groups, aryl groups and perfluorinated groups. $R_i$ is more preferably selected from the group consisting of —H, —CH$_3$, —CF$_3$ and —CH$_2$CH$_3$. Most preferably, $R_i$ is —H.

Preferably, the stabilizer compound (SC) is selected from the group consisting of formulas of compounds (A) to (G):

compound (A)

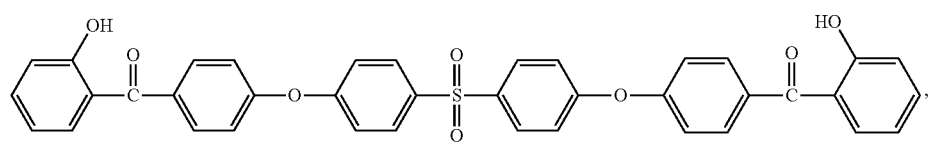

compound (B)

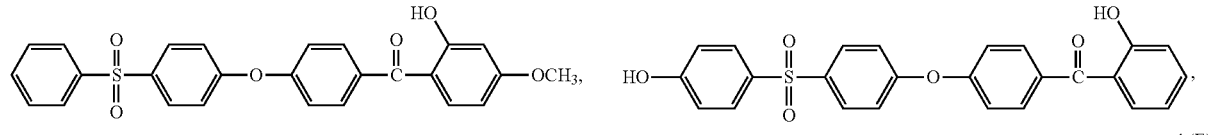

compound (C)

compound (D)

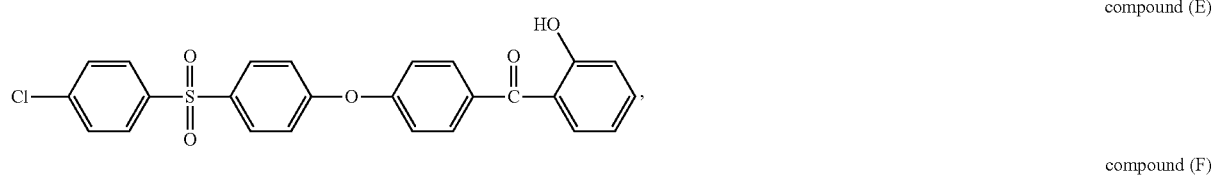

compound (E)

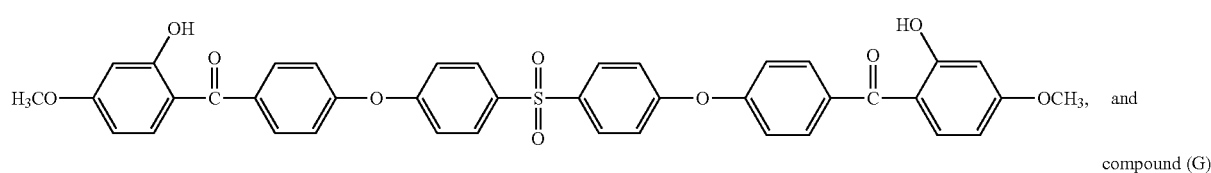

compound (F)

compound (G)

In a preferred embodiment, the stabilizer compound (SC) is selected from the group consisting of formulas of compound (A) and compound (B).

Another aspect of the present invention is directed to a method for the manufacture of said stabilizer compound (SC), which comprises the steps of:

(i) reacting compounds of formulae (III) and (IV) together to obtain compound of formula (V);

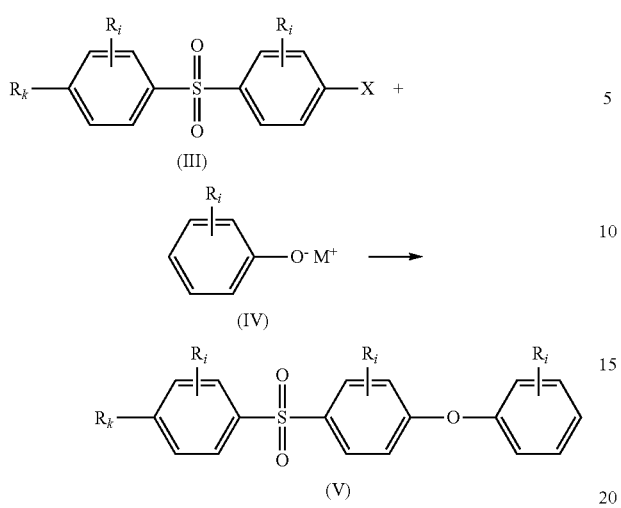

(ii) reacting compounds of formulae (V) and (VI) together in the presence of a Lewis acid to obtain compound of formula (VII);

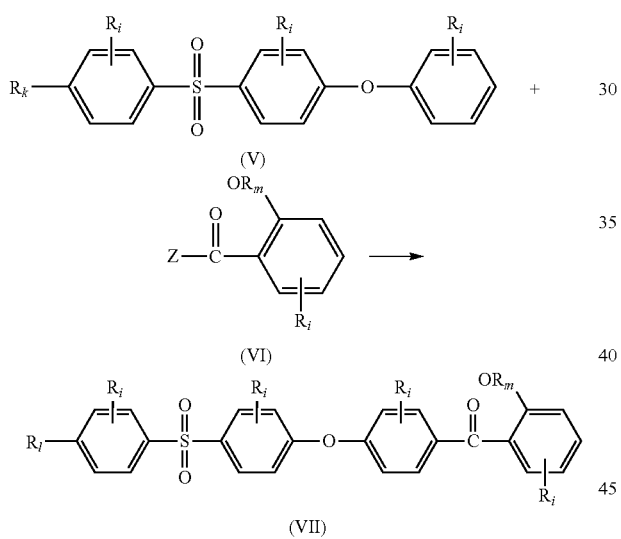

(iii) deprotecting the alkoxy moiety —OR$_m$ in compound of formula (VII) to obtain compound of formula (I):

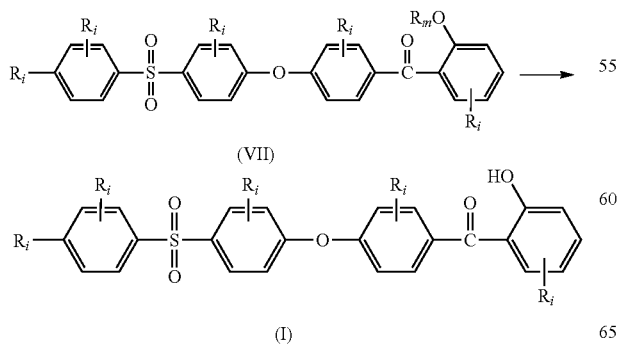

wherein:
all R$_i$, same or different from each other and from R$_j$ and R$_k$, are selected from the group consisting of —H, —NO$_2$, alkyl groups, alkoxy groups, perfluorinated groups, aryl groups, aryl amine groups, aryl ether groups, aryl sulfone groups, aryl thioether groups, and fused aryl ring systems,
R$_k$ is selected from:
  a first group consisting of a —H, a halogen, a carboxylic ester, an acid halide, an anhydride, an amide, and a thioester, or
  a second group consisting of a hydroxyl, an amine, a carboxylic acid, a thiol, and any protected derivatives thereof, or
  a moiety of formula (VIII):

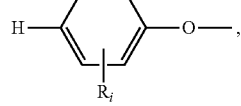

a moiety of formula (IX):

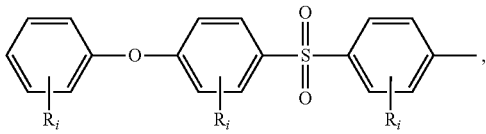

wherein R$_i$ is as above described,
R$_j$ is as defined above for formula (I),
X and Z are independently selected from halogens,
M is selected from the group consisting of a metal, an alkali metal or —H, and
R$_m$ is an alkyl group.

In the formulas (III), (IV), (V) and (VII), the nature of the R$_i$'s are as defined above for formula (I), including all preferred embodiments.

In the formula (VII), the nature of the R$_j$ is as defined above for formula (I), including all preferred embodiments.

In the formulas (III) and (V), R$_k$ is preferably selected from:
  a first group consisting of a —H, a halogen, an acid halide, and an anhydride, or
  a second group consisting of a hydroxyl, an amine, a carboxylic acid, a thiol, and any protected derivatives thereof, or
  a moiety of formula (VIII):

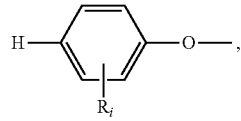

wherein R$_i$ is as above described.

In the formulas (III) and (IV), X and Z may be the same or different and are preferably selected —Cl, —F and —Br. Most preferably, X and Z are —Cl.

M preferably selected from the group consisting of H, Na, Li, K,

Non-limitive example of $R_m$ are notable —$CH_3$, —$CH_2CH_3$, —$(CH_2)_5CH_3$, $(CH_2)_7CH_3$, —$CH_2OCH_3$, —$(CH_2)_2OCH_3$, and

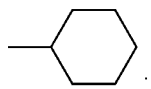

Most preferably, $R_m$ is —$CH_3$.

The step (i) is preferably carried out in a polar aptotic solvent, preferably selected from tetrahydrofuran, dimethylsulfoxide, dimethylsulfone, diphenylsulfone, diethylsulfoxide, diethylsulfone, diisopropylsulfone, sulfolane and tetrahydrothiophene-1-monoxide, dimethylacetamide, dimethylformamide, N-methyl pyrrolidone and mixtures thereof. Excellent results were obtained when using sulfolane.

The steps (ii), and (iii) are also preferably carried out in a polar aptotic solvent, preferably selected from chloroform, dichloromethane, diethylether, hexane, toluene, 1,2-dichloroethane and mixtures thereof. Excellent results were obtained when using 1,2-dichloroethane.

The step (i) is preferably carried out at a temperature of between 140° C. and 250° C. at atmospheric pressure, more preferably between 170 and 230° C. and most preferably between 190 and 220° C.

The steps (ii) and (iii) are preferably carried out at a temperature of between 0° C. and 50° C. at atmospheric pressure, more preferably between 10 and 40° C. and most preferably between 15 and 35° C. Excellent results were obtained when the reactions were carried out at room temperature.

The step (ii) involving compounds of formulae (V) and (VI) occurs in the presence of a Lewis acid to obtain compound of formula (VII). The Lewis acid is preferably selected from the group consisting of $AlCl_3$, $AlBr_3$, $BCl_3$, $BF_3$, $FeBr_3$, $FeCl_3$, $SnCl_4$, and $TiCl_4$. Excellent results were obtained when using $AlCl_3$.

In the formulas (III) and (V), the $R_k$ may be selected from a second group consisting of a hydroxyl, an amine, a carboxylic acid, a thiol, and any protected derivatives thereof. The term "protected derivative" is intended to denote the product of a reaction between the compound of formula (IV) where Y is a hydroxyl, an amine, a carboxylic acid, or a thiol and a protecting group. The protected derivative can then undergo a chemoselective reaction with compound of formula (III) to lead to the compound of formula (I) after a further step of deprotection. These protection/deprotection steps may be carried out in various conditions, which are well known of the one skilled in the art. Examples of the protecting group of hydroxyl groups include an acetyl group, a methoxyethyl group, and a tetrahydropyranyl group. Examples of the protective group of amino groups include a tert-butoxycarbonyl group, a benzyloxycarbonyl group, and a phthaloyl group. Examples of the protective group of carboxyl groups include a methyl group, an ethyl group, a benzyl group, a p-nitrobenzyl group, a tert-butyl group and a cyclohexyl group.

The use of a protected derivative in $R_k$ in formulas (III) and (V) may be sometimes advantageous to prevent, if necessary, the disubstitution of the compound of formula (III) with the compound of formula (IV).

The Applicant has found out that the stabilizer compound (SC) according to the present invention can be used as a powerful light stabilizer for polymers either per se, i.e. in a blend with a polymer (P*), or when used as an end-capper of a polymer (P).

Therefore, still another aspect of the present invention is directed to an end-capped stabilized polymer (ESP) comprising recurring units and at least two chain ends, wherein at least one of the chain ends comprises the moiety of the general structural formula (X):

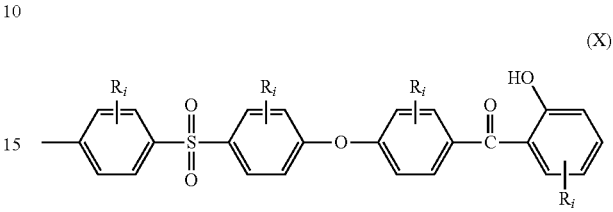

(X)

wherein:
all $R_i$ are as above defined for formula (I), including all preferred embodiments.

Yet another aspect of the present invention relates to a method for the manufacture of the end-capped stabilized polymer (ESP) comprising the step of reacting the stabilizer compound (SC) of the general structural formula (I) where Rj is selected from:
  a first group consisting of a —H, a halogen, a carboxylic ester, an acid halide, an anhydride, an amide, and a thioester, and
  a second group consisting of a hydroxyl, an amine, a carboxylic acid, a thiol, and any protected derivatives thereof,
with at least:
  a polymer (P) comprising at least one reactive chain end able to react with the $R_j$ of the general structural formula (I), or
  a monomer (M) comprising at least two reactive groups; of which at least one is able to react with the $R_j$ of the general structural formula (I).

The term "reactive chain end or group able to react with the $R_j$ of the formula (I)" is intended to denote that the polymer (P) or the monomer (M) comprise at least one accessible functional group able to form, after its chemical reaction with the $R_j$ of the stabilizer compound (SC) of the general structural formula (I), a covalent bond. Typically, this reaction may be a condensation or a transesterification. As discussed above, the $R_j$ is selected from a first group consisting of a halogen, a carboxylic ester, an acid halide, an anhydride, an amide, and a thioester or from a second group consisting of a hydroxyl, an amine, a carboxylic acid, a thiol, and any protected derivatives thereof. The one skilled in the art will recognize that the nature of the available functional group on the polymer (P) or the monomer (M) may vary depending on the nature of the $R_j$.

For example, table 1 gives a list of possible reactive chain ends/groups which are able to react with the $R_j$ of the general structural formula (I).

TABLE 1

Some possible combinations of reactive chain ends with $R_j$ in the invented method

| Reactive chain ends/groups | $R_j$ |
|---|---|
| a hydroxyl | a halogen, a carboxylic ester, an acid chloride, an anhydride, or a carboxylic acid |

TABLE 1-continued

Some possible combinations of reactive chain ends with
$R_j$ in the invented method

| Reactive chain ends/groups | $R_j$ |
|---|---|
| a halogen | a hydroxyl or a thiol or an amine |
| a carboxylic acid | an amine, an alcohol, or a thiol |
| an amine | an acid halide, a carboxylic acid, an anhydride, or a carboxylic ester |
| an amide | an amide |
| a carboxylic ester | a carboxylic ester, a hydroxyl, an amine, or a thiol |

Therefore, the at least one reactive chain end or the at least one reactive group is able to react with the $R_j$ is preferably selected from the group consisting of a hydroxyl, a halogen, a carboxylic acid, and an amine.

The level of end capping of the stabilizer compound (SC) of the general structural formula (I) on the obtained end capped stabilized polymer (ESP) can thus be controlled via the quantity of the stabilizer compound (SC) used, its reactivity, the reaction conditions and whether the stabilizer compound (SC) is introduced on the polymer (P) or during the polymerization of the monomer (M).

A wide range of polymers (P) may be used in the present invention, as long as they contain at least one chain end able to react with the $R_j$ of the general structural formula (I).

The polymer (P) comprising at least one reactive chain end is advantageously an aromatic polymer comprising more than 35 mol %, preferably more than 45 mol %, more preferably more than 55 mol %, still more preferably more than 65 mol % and most preferably more than 75 mol % of recurring units which are aromatic recurring units, based on the total number of moles of recurring units in the polymer (P). For the purpose of the present invention, the expression "aromatic recurring unit" is intended to denote any recurring unit that comprises at least one aromatic group in the main polymer backbone.

In certain embodiments, the polymers (P) advantageously comprise at least 5, preferably at least 10 recurring units. On the other hand, the polymers of the polymer composition (C) advantageously comprise at most 20, preferably at most 15 recurring units.

In certain other embodiments, the polymers (P) advantageously comprise at least 50, preferably at least 100 recurring units. On the other hand, the polymers (P) advantageously comprise at most 300, preferably at most 300 recurring units.

The polymer (P) may be a semi-crystalline polymer or an amorphous polymer. Semi-crystal line polymers (P) may typically have glass transition temperatures of at least 120° C., preferably at least 140° C. and melting temperatures generally greater than 250° C., preferably greater than 300° C.

Amorphous polymers (P) typically have a glass transition temperature of at least 140° C., more typically of at least 150° C. and up to 200° C. Glass transition temperature (Tg) and melting temperature (Tm) are generally determined by DSC, according to ASTM D3418.

The polymer (P) may notably be selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene, styrene acrylonitrile, acrylate styrene acrylonitrile, cellulosic acetate butyrate, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

Among the more preferred polymers (P), one may cite the aromatic poly(sulfone)s, aromatic poly(ether ketone)s such as poly(ether ether ketone)s (PEEK), aromatic poly(amide)s, aromatic poly(imide)s, poly(phenylene)s, and aromatic liquid crystalline polymers.

Aromatic poly(sulfone)s include notably polyphenylsulfone, polysulfone, polyethersulfone, and polyetherethersulfone, the structural repeat units of which are listed below:

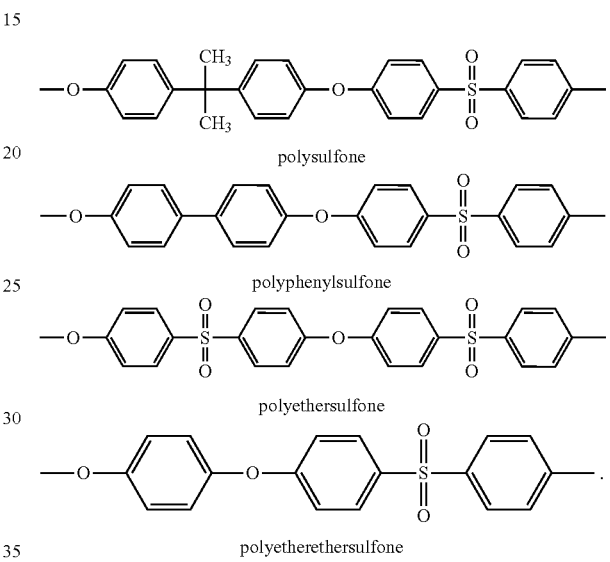

polysulfone polyphenylsulfone polyethersulfone polyetherethersulfone

Aromatic poly(ether ketone)s include notably poly(etherketone), poly(etheretherketone) and poly(etherketoneketone), the structural repeat units of which are listed below Polyetherketone Polyetheretherketone Polyetherketoneketone When the method for the manufacture of the end capped stabilized polymer (ESP) comprises the step of reacting the stabilizer compound (SC) of the general structural formula (I) with at least a polymer (P) comprising at least one reactive chain end, the reaction can take place at the end of the polymerization reaction of the polymer (P) or after the polymer (P) has been isolated.

Among methods for the manufacture of the end capped stabilized polymer (ESP) comprising the step of reacting the stabilizer compound (SC) of the general structural formula (I) with at least a polymer (P) comprising at least one reactive chain end, one can mention a method comprising a step of comprising the reactive extrusion where the stabilizer compound (SC) of formula (I) is extruded with at least one polymer (P) to obtain the end capped stabilized polymer (ESP).

In addition to the above described polymer (P), at least one monomer (M) can also be used in the method for the manufacture of the end capped stabilized polymer (ESP) according to the present invention, as long as it contains at least two reactive groups: of which at least one is able to react with the $R_j$ of the general structural formula (I).

Monomers (M) include notably di-(4-fluoro-phenyl)sulfone, di-(4-chloro) phenyl)sulfone, 4,4'-biphenol; hydroquinone, 4,4'-dihydroxybiphenyl, resorcinol, dihydroxynaphthalene (2,6 and other isomers), 4,4'-dihydroxydiphenyl ether or -thioether, 4,4'-dihydroxybenzophenone, 2,2'-di-(4-hydroxyphenylpropane (bisphenol A) or -methane, 4,4'-oxybis(phenol), and hexafluoroisopropylidene diphenol. Di-(4-fluoro-phenyl)sulfone and 4-4'-biphenol are preferred as monomer (M).

When the method for the manufacture of the end capped stabilized polymer (ESP) comprises the step of reacting the stabilizer compound (SC) of the general structural formula (I) with at least a monomer (M) comprising at least two reactive groups, the reaction advantageously takes place in the presence of a polar aproric solvent, including notably tetrahydrofurane (THF), N,N-dimethylformamide (DMF), N,N-dimethylacetamide (DMAc), N-methyl-2-pyrrolidone, diphenylsulfone, and toluene. The stabilizer compound (SC) of the general structural formula (I) and the at least one monomer (M) may be contacted together in any order.

The reaction temperature is generally higher than 80° C., preferably higher than 120° C., more preferably higher than 140° C. The polymerization is generally carried out for a duration exceeding one hour, and the duration of the polymerization may exceed 10 hours.

The reaction also advantageously takes place in the presence of a base such as an alkaline metal salt, for instance, potassium or sodium carbonate.

Thus, another aspect of the present invention relates to a polymer composition (C), comprising at least one of the above disclosed stabilizer compounds (SC) and at least one polymer (P*). The polymer (P*) of the polymer composition (C) may be the same than the above mentioned polymer (P) (including all preferred embodiments), except for the fact that it does not have to (but may) contain at least one chain end able to react with the $R_j$.

The polymer composition (C) may also further comprises at least another ingredient selected from the group consisting of dyes, pigments, fillers, UV stabilizers, light stabilizers, optical brighteners.

The polymer composition (C) comprises advantageously at least 0.01 wt. %, preferably at least 0.05 wt. %, more preferably at least 0.1 wt. %, still more preferably at least 0.5 wt. % and most preferably at least 1 wt. % of the stabilizer compounds (SC), based on the total weight of the polymer composition (C). Also, the polymer composition (C) comprises advantageously at most 15 wt. %, preferably at most 10 wt. %, more preferably at most 8 wt. %, still more preferably at most 5 wt. % and most preferably at most 3 wt. % of the stabilizer compounds (SC), based on the total weight of the polymer composition (C).

When no other ingredient than the stabilizer compound (SC) and the at least one polymer (P*) are present, the polymer composition (C) comprises advantageously at least 20 wt. %, preferably at least 30 wt. %, more preferably at least 40 wt. %, still more preferably at least 50 wt. % and most preferably at least 60 wt. % of the at least one polymer (P*), based on the total weight of the polymer composition (C). Also, the polymer composition (C) comprises advantageously at most 99.99 wt. %, preferably at most 99.95 wt. %, more preferably at most 99.90 wt. %, still more preferably at most 99.5 wt. % and most preferably at most 99 wt % of the at least one polymer (P*), based on the total weight of the polymer composition (C).

The polymer composition (C) may further comprise at least one additional stabilizer selected from the group consisting of 2-(2'-hydroxyphenyl) benzotriazoles, oxamides, 2-(2 hydroxyphenyl)1,3,5-triazines, other 2-hydroxybenxophenone derivatives, cyanoacrylates, benzo-oxazolines, benzoxazinones, and hindered phenolic antioxidants.

It may be advantageous to further incorporate in the polymer composition (C) hindered amine light stabilizers ("HALS"). Examples of such HALS are (2,2,6,6-tetramethylpiperidyl) sebacate, (2,2,6,6-tetramethylpiperidyl-) succinate, condensate of 1-hydroxyethyl-2,2,6,6-tetramethyl-4-hydroxypiperidine and succinic acid, condensate of N,N'-bis(2,2,6,6-tetramethyl-1-4-piperidyl) hexamethylene diamine and 4-tert-octylamino-2,6-dichloro-1,3,-5-s-triazine, tris(2,2,6,6-tetramethyl-4-piperidyl) nitrilotriacetate, tetrakis (2,2,6,6-tetramethyl-4-piperidyl) 1,2,3,4 butanetetraoate, 1,1'-(1,2-ethanediyl)-bis(3,3,5,5-tetramethylpiperazinone),4-benzoyl-2,2,6,6 tetramethylpiperidine, 4-stearyloxy-2,2,6,6-tetramethyl piperidine, to (1,2,2,6,6-pentamethylpiperidyl) 2-n-butyl-2 (2-hydroxy-3,5-di-tert-butylbenzyl) malonate, 3-n-octyl-7,7,9,9-tetramethyl-1,3,8-triazas-piro[4.5]decane-2,4-dione, to (1-octyloxy-2,2,6,6-tetramethylpiperidyl) sebacate, (1-octyloxy-2,2,6,6-tetramethylpiperidyl) succinate, condensate of N,N'-bis (2,2,6,6-tetramethyl-4-piperidyl) hexamethylenediamine, and compounds with similar chemical structures. As with the stabilizer compounds (SC) of the present disclosure, the HALS may be incorporated in the polymer composition (C) in conventional amounts, generally higher than 0.05 wt. % and preferably higher than 0.1 wt. %; further, these amounts are generally lower than 5 wt. % and preferably lower than 1 wt. %.

Further in accordance with the present disclosure, the polymer composition (C) may also contain a variety of other polymer additives in addition to the stabilizer compounds of the present disclosure. These additives may include fillers in spherical, spheroidal or polyhedral form, collectively known as "ingredients" herein. Among these other fillers, calcium carbonate, calcium sulfate, barium sulfate, glass beads, ceramic beads, antimony trioxide, zinc borate, and other metal salts and oxides, can be utilized.

Other optional conventional ingredients of the complete polymer composition (C) include nucleating agents such as silica, adhesion promoters, compatibilizers, curing agents, lubricants, mold release agents, dyes and colorants, smoke-suppressing agents, heat stabilizers, antioxidants, UV absorbers, tougheners such as rubbers, plasticizers, antistatic agents, melt viscosity depressants such as liquid crystalline polymers, and compounds of similar structures. The choice of fillers and other ingredients in the final polymer composition (C) including the stabilizer compounds of the present disclosure will depend primarily on the intended use for the articles of manufacture.

The components of the polymer composition (C) along with the optional additional ingredients may be incorporated into the polymer composition (C) by a variety of different methods and procedural steps which aim to provide their collective improvement in stability properties throughout the mixture. For example, it is possible to incorporate the above mentioned components and optional additional ingredients by mixing them into the polymer at an early processing stage, or at the start or at the end of the synthesis reaction, or in a subsequent compounding process. A certain method comprises dry mixing the essential components and optional ingredients in powder or granular form, in appropriate proportions, using e.g. a mechanical blender, such as a drum blender and compounds of similar structures. The mixture is then melted batch-wise or in a continuous device, e.g. extruders and compounds of similar structures, extruding the mixture into strands and chopping the strands into pellets. The mixture to be melted may also be prepared by well-known master-batch methods. The continuous melting device may also be fed with the components and ingredients of the polymer composition (C) added separately without dry premixing. A certain other method comprises dissolving the polymer(s) in one or more organic solvents then causing the dissolved polymer(s) to precipitate by the addition of a non-solvent, and finally molding the recovered dried cake.

Of particular use tor the polymer composition (C) of the present invention is the manufacture of shaped articles. Therefore, another aspect of the present invention relates to an article comprising the polymer composition (C).

contains at least one chain end able to react with the above mentioned $R_j$ of formula (I), and wherein the polymer (P*) may be the same than the polymer (P), except for the fact that it does not have to (but may) contain at least one chain end able to react with the $R_j$ of formula (I).

In particular, the at least one stabilizer compound (SC) may act as an acid scavenger for the at least one polymer (P) or (P*).

The disclosure will now be illustrated with working examples, which are intended to illustrate the working disclosure and not intended to take respectively to imply any limitations on the scope of the present disclosure.

EXAMPLES

Materials:
Udel® PSU polysulfone, available from Solvay Specialty Polymers USA, L.L.C.
Compounds (A) and (B), two stabilizer compounds according to the invention, which synthesis are disclosed below, having respectively the following chemical structures:

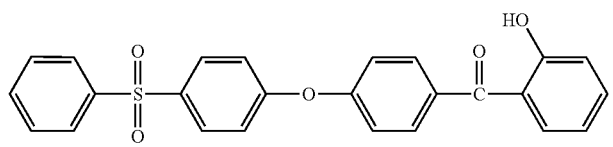

Compound (A)

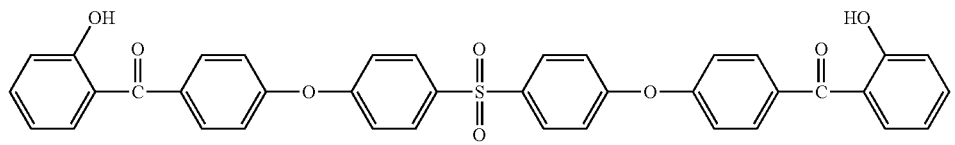

Compound (B)

Indeed, the outstanding balance of advantageous properties featured by the polymer compositions (C) of the present invention in connection with their high glass transition temperature, thermal stability, flame resistance, chemical resistance and melt processability, makes them particularly suitable for the manufacture, by any known processing method, of various articles. The article of the present invention may be produced by extrusion or molding techniques.

Various molding techniques may be used to form shaped articles or parts of shaped articles from the polymer composition (C). Powders, pellets, beads, flakes, reground material or oilier forms of the polymer composition (C) may be molded, with or without liquid or other additives, pre mixed or fed separately. The polymer composition (C) may notably be molded into a film, a sheet, a fiber, a foam or any molded article suitable for indoor and outdoor applications.

A last aspect of the present invention relates to a method for stabilizing a polymer (P) or (P*) comprising adding at least one stabilizer compound (SC) or at least one end-capped stabilized polymer (ESP) to at least one polymer (P) or to at least one polymer (P*), wherein the polymer (P), Commercial stabilizers belonging to the same 2-hydroxybenzophenone class than compounds (A) and (B), namely, Chimasorb® 81, available from BASF, and Lowilite® 24, available from Addivant USA, having respectively the following chemical structures:

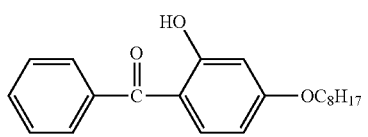

Chimasorb® 81

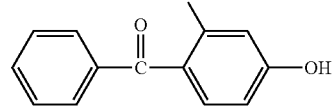

Lowilite® 24

Synthesis and Characterization of Stabilizer Compound (A)
The compound (A) was prepared in two steps:

Synthesis of 1-phenoxy-4-(phenylsulfonyl)benzene

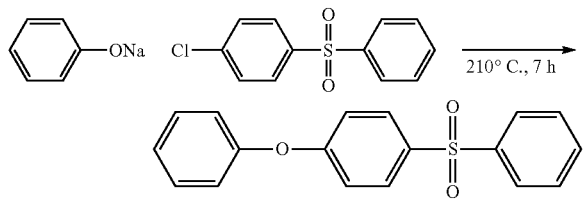

4-Chloradiphenyl sulfone (20.00 g, 0.0791 mol), sodium phenolate (8.41 g, 0.0495 mol, and sulfolane (100 mL), were combined, heated to 210° C. for 7 h, and then cooled to ca. 60° C., at which point the reaction mixture was diluted with $H_2O$ (500 mL), and extracted with $CH_2Cl_2$ (3×250 mL). The combined organic layers were then dried over anhydrous $MgSO_4$, filtered, and the solvent wax removed in vacuo to afford a viscous yellow oil that, upon standing overnight, solidified. Following recrystallization from ethanol/water pure, 1-phenoxy-4-(phenylsulfonyl)benzene (4.23 g, 57.94%) was isolated as a white crystalline solid. $^1$H NMR ($CDCl_3$): δ=7.93 (m, 2H, $SO_2ArH$), 7.88 (m, 2H, $SO_2ArH$), 7.57-7.46 (m, 3H, OArH+ArH), 7.39 (m, 2H, OArH), 7.21 (m, 1H, ArH), 7.04-6.99 (m, 4H, OArH+ArH). $^{13}$C NMR ($CDCl_3$): δ=162.1 (1C, $CH_{Ar}O$) 154.8 (1C, $C_{Ar}O$), 142.0 (1C, $SO_2C_{Ar}$), 134.9 (1C, $SO_2C_{Ar}$), 133.0 (1C, $CH_{Ar}$), 130.1 (2C, $CH_{Ar}$), 129.9 (2C, $CH_{Ar}$), 129.2 (2C, $CH_{Ar}$), 127.4 (2C, $CH_{Ar}$), 125.0 (1C, $CH_{Ar}$), 120.3 (2C, $CH_{Ar}$), 117.6 (2C, $CH_{Ar}$). HRMS (ASAP with APCI): m/z 311.0818 (M+H, calculated, for $C_{18}H_{14}O_3S$ 311.0742).

Synthesis of (2-hydroxyphenyl)(4-(4-(phenylsulfonyl)phenoxy)phenyl)methanol

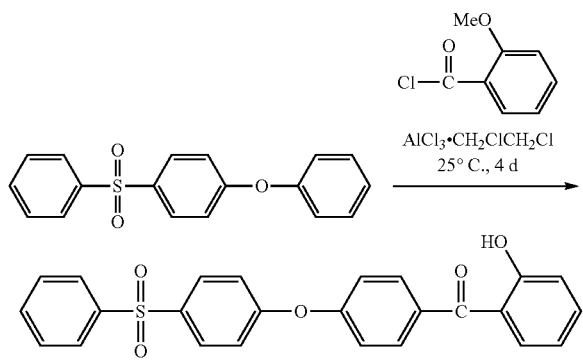

A solution of o-anisoyl chloride (27.45 g, 0.161 mol) was dissolved in 1,2-Dichlorethane (100 mL) and added dropwise to a nitrogen purged reaction vessel containing $AlCl_3$ (27.45 g, 0.2055 mol), 1-phenoxy-4-(phenylsulfonyl)benzene (5 g, 0.0161 mol) and 1,2-Dichlorethane (100 mL). Upon complete addition, the reaction was allowed to stir at for 4 days at 25° C. Subsequently, $H_2O$ (125 mL) was added, then 1 N HCL (125 mL), and the mixture was then extracted with $CH_2Cl_2$ (3×200 mL). The combined organic layers were rotovapped to dryness to afford a dark solid that was stirred with 1 N KOH (300 mL) and $CH_2Cl_2$ (200 mL) for 2 h at 25° C. to convert un-reacted carboxylates to water soluble sodium carboxylate salts. This mixture was then extracted with dichloromethane (2×200 mL) and organic layers were combined, dried over anhydrous $MgSO_4$, filtered, and the solvent removed to afford a viscous, dark orange, oil comprised predominately of the deprotected 2-hydroxybenzophenone derivative as determined using thin layer chromatography (TLC) ($SiO_2$, eluent: 1:2 ethyl acetate/hexane, $R_f$=0.54). The final product, (2-hydroxyphenyl)(4-(4-(phenylsulfonyl)phenoxy)phenyl) methanol (3.25 g, 47%), was isolated via column chromatography ($SiO_2$ eluent: 1:3 ethyl acetate/hexane gradient with 1:2 ethyl acetate/hexane) as a light yellow solid, $^1$H NMR (DMSO-d6): δ=10.35 (s, 1H, OH), 7.99 (m, 4H, $SO_2CCH_{Ar}$), 7.78 (m, 2H, O=$CCCH_{Ar}$), 7.70 (m, 1H, O=$CCCH_{Ar}$), 7.63 (m, 2H, $CH_{Ar}$), 7.43 (m, 1H, $CH_{Ar}$), 7.34 (m, 1H, $CH_{Ar}$), 7.25 (m, 4H, $CH_{Ar}$), 6.95 (m, 2H, $CH_{Ar}$. HRMS (ASAP with APCI): m/z 431.1024 (M+H, calculated for $C_{25}H_{19}O_5S$ 431.0953).

Synthesis and Characterization of Stabilizer Compound (B)
The compound (B) was also prepared in two steps:

Synthesis of 4,4'-sulfonylbis(phenoxybenzene)

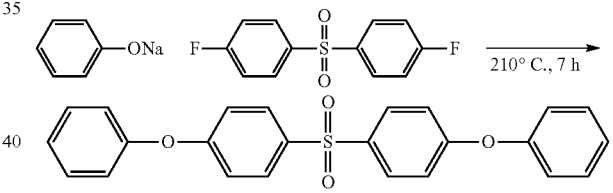

4-4' difluorodiphenylsulfone (20.00 g, 0.0786 mol), sodium phenolate (36.75 g, 0.3166 mol, and sulfolane (100 mL), were combined and heated to 200° C. for 5 h at which point the reaction was checked using GC-MS, which showed 100% conversion to the desired product with no detectable concentration of the monosubstituted product. Following cooling to 25° C., the reaction mixture was then diluted with 1 N KOH (250 mL) and the crude product was extracted from the resulting aqueous emulsion using $CH_2Cl_2$ (3×200 mL). The combined organic layers were then dried over anhydrous $MgSO_4$, filtered, and the solvent was removed in vacuo to afford a semisolid that was triturated with and $EtOH/H_2O$ mixture (400 mL/10 mL) to give 4,4'-sulfonylbis(phenoxybenzene) (27.44 g, 86.75%) as a white powder that was collected via suction filtration and later dried on high vacuum. $^1$H NMR (DMSO-d6): δ=7.91 (m, 4H, $SO_2CArH$), 7.46 (m, 4H, OCArH), 7.27 (m, 2H, ArH), 7.12 (m, 8H, OCArH+ArH). HRMS (ASAP with APCI): m/z 403.1083 (M+H, calculated for $C_{24}H_{19}O_4S$ 403.1004).

Synthesis of (((sulfonylbis(4,1-phenylene))bis(oxy))bis(4,1-phenylene))bis((2-hydroxphenyl)methanone)

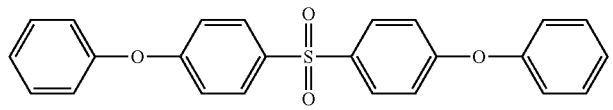

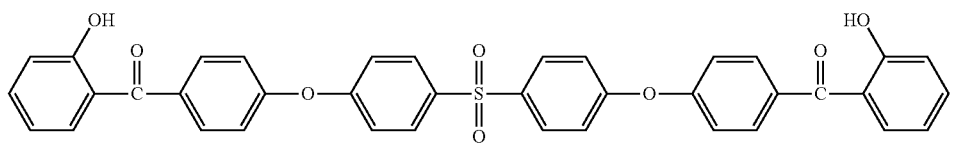

A solution of o-anisoyl chloride (42.30 g, 0.248 mol) was dissolved in 1,2-Dichlorethane (100 mL) and added dropwise to a nitrogen purged reaction vessel containing AlCl$_3$ (33 g, 0.248 mol), 4,4'-sulfonylbis(phenoxybenzene) 4,4'-sulfonylbis(phenoxybenzene) (5 g, 0.0161 mol) and CH$_2$ClCH$_2$Cl (100 mL). Upon complete addition, the reaction was allowed to stir at for 2 days at 25° C. Subsequently, H$_2$O (100 mL) was added, then 1 N HCL (100 mL, pH=0), and the mixture was then extracted with CH$_2$Cl$_2$ (3×200 mL). The combined organic layers were rotovapped to dryness to afford a dark solid that was stirred with 1 N KOH (300 mL) and CH$_2$Cl$_2$ (200 mL) for 2 h at 25° C. to convert un-reacted carboxylates to water soluble sodium carboxlyate salts. This mixture was then extracted with CH$_2$Cl$_2$ (2×200 mL) and organic layers were combined, dried over anhydrous MgSO$_4$, filtered, and the solvent removed to afford a viscous, dark orange, oil comprised of a mixture of deprotected and methoxy protected 2-hydroxy-benzophenones as determined using TLC (SiO$_2$, eluant: 1:2 ethyl acetate/hexane). To convert the protected 4,4'-sulfonylbis2-methoxybenzophenone to the desired deprotected 4,4'-sulfonylbis2-hydroxybenzophenone, the product mixture was dissolved in toluene (125 mL), treated by the addition of solid AlBr$_3$ (14.32 g, 0.0537 mol), and the resulting mixture was then heated to reflux for 1 h, cooled to room temperature, and stirred at 25° C. overnight. Subsequently, the reaction mixture was treated with 1 M HCl (375 mL) to neutralize any residual AlBr$_3$ and was then stirred for 1 h at 25° C. at which point the aqueous layer was extracted with toluene (3×100 mL) and separated. The combined organic layers were then dried over anhydrous MgSO$_4$, filtered, and the solvent removed in vacuo to afford a dark viscous oil. Purification via column chromatography (SiO$_2$, eluant: 1:3 ethyl acetate/hexane gradient with 1:2 ethyl acetate/hexane, R$_f$=0.48), afforded pure (((sulfonylbis(4,1-phenylene))bis(oxy))bis(4,1-phenylene))bis((2-hydroxyphenyl)methanone) as a pale yellow solid (3.7 g, 48.2%). $^1$H NMR (DMSO-d6): δ=10.34 (s, 2H, OH), 8.00 (m, 4H, SO$_2$CCHAr), 7.79 (m, 4H, O═CCCHAr), 7.43 (m, 2H, CHAr), 7.34 (m, 2H, CHAr), 7.28-7.22 (m, 8H, CHAr), 6.99-6.92 (m, 4H, CHAr). HRMS (ASAP with APCI): m/z 642.1192 (M+, calculated for C$_{38}$H$_{26}$O$_8$S 642.1348).

UV stability of films of Udel® PSU polysulfone containing 5 mol. % of compounds (A) and (B) and the two commercial 2-hydroxybenzophenone stabilizers, Chimasorb® 81 and Lowilite® 24.

Solution blending an film preparation for weathering experiments: the polysulfone was solution blended with stabilizer compound (A) at 5 mol % loading, based on the total number of moles of recurring units in the polymer. This was accomplished by first dissolving 0.266 g of the stabilizer compound (A) and 5.00 g of polymer in NMP to prepare a 25 wt. % solution containing thus 5.04 wt. % of the stabilizer compound (A), followed by film casting onto a glass plate pre-heated to 100° C. using a 15 mil side of a square applicator (BYK Gardener). The resulting 4"×4"×50 micron thick film was dried (on a glass plate) using a vacuum oven (120° C., >25 mmHg) for 48 h, at which point the film was removed from the glass substrate using a razor blade. The free-standing film was then cut into 10 mm×100 mm×50 µm thick strips using a precision trammel cutter and mounted onto an aluminum frame designed for use in an Atlas ci4000 Xenon weather-o-meter. The same procedure was applied to prepare films comprising 5 mol. % of compound (B), Chimasorb® 81 and Lowilite® 24.

UV Weathering: All weathering experiments were carried out in 24/48 hour increments for up to 5 days using an Atlas ci4000 Xenon weather-o-meter which was also further equipped with a Type "S" borosilicate inner filter and a soda lime outer filter. The cut-off filters eliminated all wavelengths above 340 nm. All weathering cycles were set for an irradiance of 0.30 w/m$^2$, with a panel temperature of 55° C., a chamber temperature of 38° C., and a RH 55%. All other variables were controlled in accordance with ASTM G155-4.

Measure of UV Stability: Following exposure to UV light via the weatherometer conditions described above, each film was subsequently placed in a UV Vis spectrophotometer set to transmission mode and the UV-Vis spectra was collected. The change in % Transmission as a function of exposure time was determined at 400 nm as a measure of the extent of UV degradation of the polymeric film at a particular exposure time. The lower the % transmission, the more the film had degraded upon exposure to UV light.

TABLE 1

Transmission (%) vs. UV exposure time of films of Udel ® PSU with and without stabilizers

| UV Exposure Time (days) | Udel ® PSU | Udel ® PSU + compound (A) | Udel ® PSU + compound (B) | Udel ® PSU + Chimasorb ® 81 | Udel ® PSU + Lowilite ® 24 |
|---|---|---|---|---|---|
| 0 | 100 | 100 | 100 | 100 | 100 |
| 1 | 88.6 | 100.9 | 100.2 | 99.6 | 99.7 |
| 3 | 83.6 | 100.4 | 99.9 | 99.6 | 99.4 |
| 5 | 79.8 | 100.5 | 99.8 | 98.7 | 98.9 |

As one may see from the data presented in table 1, the presence of the stabilizers greatly improved the UV resistance of Udel® PSU films. Interestingly, compounds (A) and (B) gave better results than the two commercial stabilizers tested for comparative purposes. Surprisingly, the presence of compound (A) even lead to transmission data which were higher than the original un-weathered film.

The thermal stabilities of the four tested stabilizers were also analyzed by measuring their volatility. This was achieved by determining the temperature at which 10 wt. % and 50 wt. % loss was observed by thermal gravimetric analysts (TGA). Results are reported in Table 2.

TABLE 2

Volatility of the compounds

| Stabilizer | Compound (A) | Compound (B) | Chimasorb ® 81 | Lowilite ® 24 |
|---|---|---|---|---|
| 10% wt. Loss | 325° C. | 419° C. | 248° C. | 232° C. |
| 50% wt. Loss | 380° C. | 483° C. | 289° C. | 278° C. |

In addition, to their demonstrated efficiency to stabilize aromatic polymers with regard to UV degradation, the stabilizer compounds according to the invention also presented the benefit of having a good thermal stability (see TGA data in Table 2). Compounds (A) and (B) behaved very differently with regard to their volatility when compared to the two commercial 2-hydroxybenzophenone stabilizers, Chimasorb® 81 and Lowilite® 24, which present a 10% wt. loss already before 300° C.

Moreover, Compound (B) also presents the further benefit of maintaining the high Tg of the high performance aromatic polymers when it is blended in them. A 5 mol % loading of Compound (B) reduced the Tg of the polymer of only about 10° C., whereas the same concentration of the two commercial 2-hydroxybenzophenone stabilizers, Chimasorb® 81 and Lowilite® 24 reduced the Tg of the same polymer of respectively 32° C. and 20° C.

The stabilizer compounds according to the invention are thus very useful for the stabilization of high performance aromatic polymers since they combine the stabilization effect with regard to UV degradation and the high temperature resistance and non-volatility under the high thermal processing temperatures of high performance aromatic polymers (i.e. as an example, the process window for sulfone polymers is ca. 300-425° C.).

The invention claimed is:

1. A stabilizer compound (SC) of the general structural formula (I):

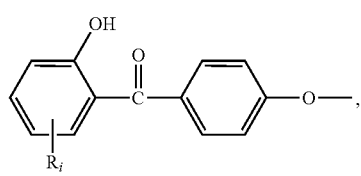

wherein:

$R_j$, same or different from $R_i$, is selected from:
  a first group consisting of a —H, a halogen, a carboxylic ester, an acid halide, an anhydride, an amide, and a thioester,
  a second group consisting of a hydroxyl, an amine, a carboxylic acid, a thiol, and any protected derivatives thereof,
  a moiety of formula (II):

(II)

[structure]

or a moiety of formula (II*):

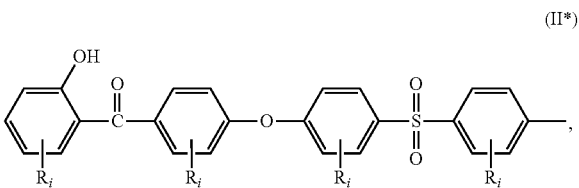

and $R_i$, same or different from each other and from $R_j$, are selected from the group consisting of —H, —NO$_2$, alkyl groups, alkoxy groups, perfluorinated groups, aryl groups, aryl amine groups, aryl ether groups, aryl sulfone groups, aryl thioether groups, and fused aryl ring systems.

2. The stabilizer compound (SC) according to claim 1, wherein said $R_i$ are —H.

3. The stabilizer compound (SC) according to claim 1, wherein it is selected from the group consisting of compound (A) and compound (B):

compound (A)

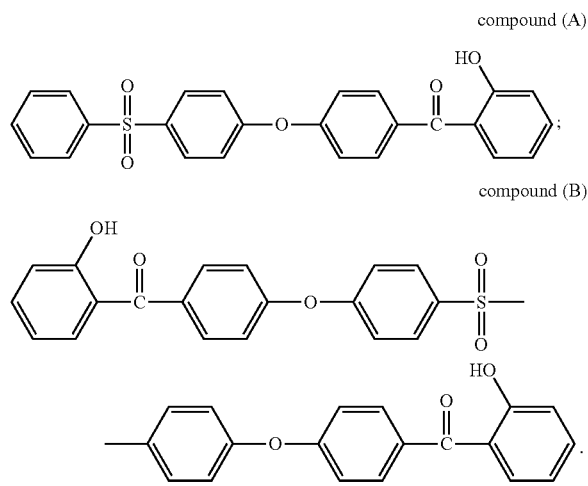

compound (B)

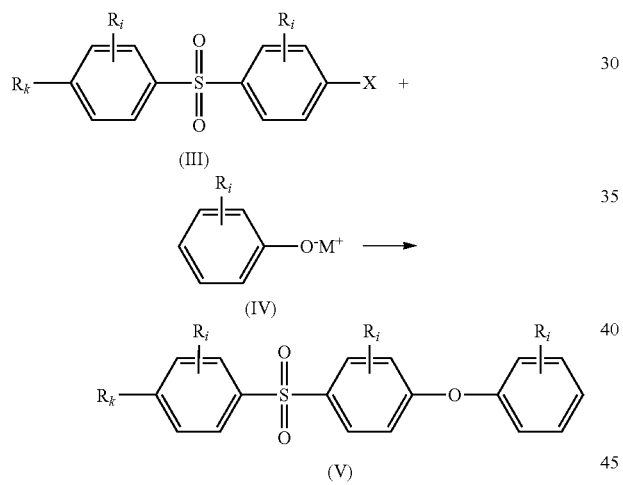

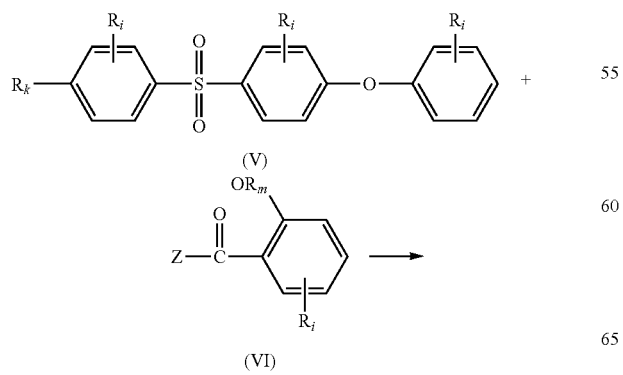

4. A method for making the stabilizer compound (SC) according to claim 1, comprising the steps of:

(i) reacting compounds of formulae (III) and (IV) together to obtain compound of formula (V);

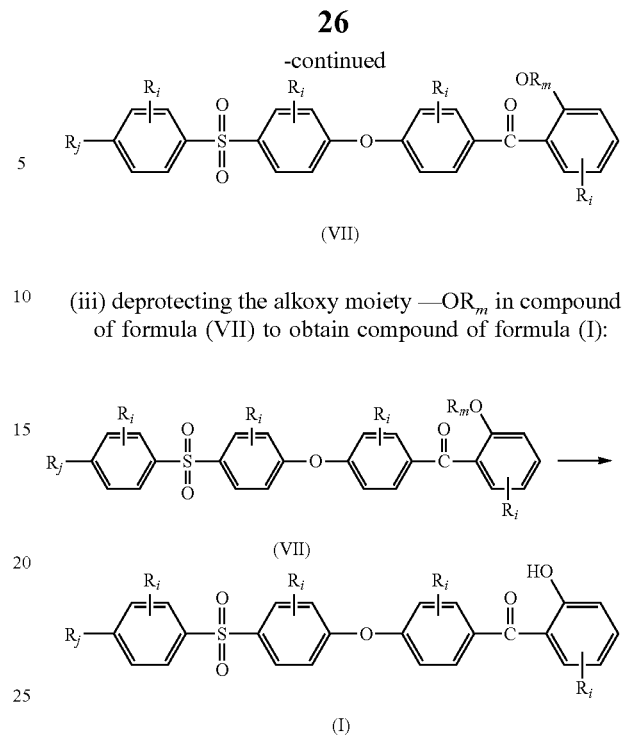

(ii) reacting compounds of formulae (V) and (VI) together in the presence of a Lewis acid to obtain compound of formula (VII);

(iii) deprotecting the alkoxy moiety —$OR_m$ in compound of formula (VII) to obtain compound of formula (I):

wherein:
all $R_i$, same or different from each other and from $R_j$ and $R_k$, are selected from the group consisting of —H, —$NO_2$, alkyl groups, alkoxy groups, perfluorinated groups, aryl groups, aryl amine groups, aryl ether groups, aryl sulfone groups, aryl thioether groups, and fused aryl ring systems, $R_k$ is selected from:
  a first group consisting of a —H, a halogen, a carboxylic ester, an acid halide, an anhydride, an amide, and a thioester, or
  a second group consisting of a hydroxyl, an amine, a carboxylic acid, a thiol, and any protected derivatives thereof, or
  a moiety of formula (VIII):

or
a moiety of formula (IX):

$R_j$ is selected from:
  a first group consisting of a —H, a halogen, a carboxylic ester, an acid halide, an anhydride, an amide, and a thioester, or a second group consisting of a hydroxyl, an amine, a carboxylic acid, a thiol, and any protected derivatives thereof, or a moiety of formula (II):

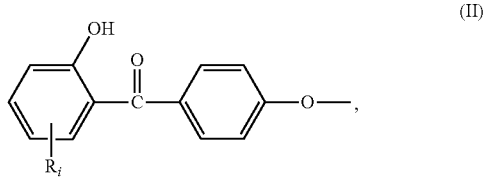

(II)

a moiety of formula (II*):

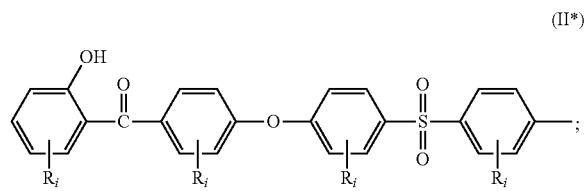

(II*)

X and Z are independently selected from halogens,

M is selected from the group consisting of a metal, an alkali metal or —H, and $R_m$ is an alkyl group.

5. The method of claim 4, wherein the steps (ii) and (iii) are carried out in a polar aprotic solvent.

6. A polymer composition (C) comprising at least one stabilizer compound (SC) according to claim 1 and at least one polymer (P*).

7. The polymer composition (C) according to claim 6, wherein the polymer (P*) is selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene polymers, styrene acrylonitrile polymers, acrylate styrene acrylonitrile polymers, cellulosic acetate butyrate polymers, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

8. The polymer composition (C) according to claim 7, wherein it further comprises at least another ingredient selected from the group consisting of dyes, pigments, fillers, UV stabilizers, light stabilizers, optical brighteners, and combinations thereof.

9. A method for stabilizing a polymer (P) or (P*) comprising adding at least one stabilizer compound (SC) according to claim 1 to at least one polymer (P) or to at least one polymer (P*), wherein the polymer (P), contains at least one chain end able to react with the Rj in formula (I) of the stabilizer compound (SC), and wherein the polymer (P*) may be the same than the polymer (P), with the proviso that it does not have to, but may optionally, contain at least one chain end able to react with the Rj of formula (I).

10. An article comprising said stabilizer compound (SC) according claim 1.

11. An article comprising said polymer composition (C) according to claim 7.

* * * * *